(12) United States Patent
Ishii

(10) Patent No.: US 12,369,784 B2
(45) Date of Patent: Jul. 29, 2025

(54) ENDOSCOPE AND INSERTION PORTION OF ENDOSCOPE INCLUDING COMPRESSED WALL PORTION, AND MANUFACTURING METHOD OF ENDOSCOPE

(71) Applicant: OLYMPUS CORPORATION, Tokyo (JP)

(72) Inventor: Kazushi Ishii, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 457 days.

(21) Appl. No.: 17/886,188

(22) Filed: Aug. 11, 2022

(65) Prior Publication Data

US 2022/0378282 A1 Dec. 1, 2022

Related U.S. Application Data

(63) Continuation of application No. PCT/JP2020/008077, filed on Feb. 27, 2020.

(51) Int. Cl.
| | |
|---|---|
| *A61B 1/00* | (2006.01) |
| *A61B 1/012* | (2006.01) |
| *A61B 1/018* | (2006.01) |
| *A61B 1/05* | (2006.01) |

(52) U.S. Cl.
CPC ............ *A61B 1/05* (2013.01); *A61B 1/00096* (2013.01); *A61B 1/012* (2013.01); *A61B 1/018* (2013.01); *A61B 1/0011* (2013.01)

(58) Field of Classification Search
USPC ........................................................ 600/130
See application file for complete search history.

(56) References Cited

U.S. PATENT DOCUMENTS

| | | | | |
|---|---|---|---|---|
| 5,305,736 A | * | 4/1994 | Ito | A61B 1/0008 600/176 |
| 8,425,407 B2 | * | 4/2013 | Sato | A61B 1/018 600/129 |

(Continued)

FOREIGN PATENT DOCUMENTS

| | | |
|---|---|---|
| JP | S59-064347 A | 4/1984 |
| JP | 2006-122498 A | 5/2006 |

(Continued)

OTHER PUBLICATIONS

Mar. 31, 2020 International Search Report issued in International Patent Application No. PCT/JP2020/008077.

*Primary Examiner* — John P Leubecker
(74) *Attorney, Agent, or Firm* — Oliff PLC

(57) ABSTRACT

An endoscope includes: a distal end constituting portion including a first hole and a second hole; a treatment instrument channel, a distal end of which is fixed in the first hole; and an adjacent unit, a distal end of which is fixed in the second hole, and is arranged side by side with the treatment instrument channel. The treatment instrument includes a first wall portion formed by compression forming such that a wall thickness of the first wall portion of the treatment instrument channel is smaller than a wall thickness of a different wall portion of the treatment instrument channel. The first wall portion is disposed on a side of the treatment instrument channel facing the adjacent unit.

20 Claims, 8 Drawing Sheets

(56) References Cited

U.S. PATENT DOCUMENTS

| | | | |
|---|---|---|---|
| 8,911,355 B2* | 12/2014 | Takeuchi | F16L 47/32 600/153 |
| 2006/0235273 A1* | 10/2006 | Moriyama | A61B 1/00188 600/113 |
| 2008/0183038 A1 | 7/2008 | Tilson et al. | |
| 2009/0295913 A1* | 12/2009 | Sato | A61B 1/0051 348/E7.085 |
| 2013/0150667 A1* | 6/2013 | Mitamura | A61B 1/00064 600/104 |
| 2013/0203287 A1* | 8/2013 | Natoli | H01R 43/00 29/857 |
| 2013/0253268 A1* | 9/2013 | Okada | A61B 1/07 600/104 |
| 2014/0255627 A1* | 9/2014 | Yamaguchi | H02G 3/0468 428/34.1 |
| 2015/0230692 A1 | 8/2015 | Matsuda et al. | |
| 2019/0092149 A1* | 3/2019 | Facchinello | B60J 7/141 |
| 2019/0151817 A1* | 5/2019 | Henriksson | A23L 3/32 |
| 2022/0369896 A1* | 11/2022 | Hirayama | A61B 1/005 |

FOREIGN PATENT DOCUMENTS

| | | |
|---|---|---|
| JP | 2009-285305 A | 12/2009 |
| WO | 2008/095046 A2 | 8/2008 |
| WO | 2008/095052 A2 | 8/2008 |
| WO | 2014/168000 A1 | 10/2014 |

\* cited by examiner

ENDOSCOPE AND INSERTION PORTION OF ENDOSCOPE INCLUDING COMPRESSED WALL PORTION, AND MANUFACTURING METHOD OF ENDOSCOPE

CROSS-REFERENCE TO RELATED APPLICATION

This application is a continuation application of PCT/JP2020/008077 filed on Feb. 27, 2020, the entire contents of which are incorporated herein by this reference.

BACKGROUND

1. Technical Field

The present disclosure relates to an endoscope, an insertion portion of the endoscope, and a manufacturing method of the endoscope. The endoscope includes an insertion portion configured to be inserted into a subject, and a distal end constituting portion provided at a distal end in a longitudinal axis direction of the insertion portion. The distal end constituting portion includes a first hole in which a treatment instrument channel is fixed and a second hole in which an adjacent unit is fixed.

2. Description of the Related Art

In recent years, endoscopes have been widely used in medical fields. An endoscope for use in the medical fields is capable of observing and picking up an image of an organ in a body cavity with an image pickup unit included in a distal end portion of an insertion portion of the endoscope by inserting the insertion portion having an elongated shape into the body cavity as a subject.

Further, the endoscope for use in the medical fields is capable of performing various kinds of treatments such as resection of a tissue in a body cavity by using, as needed, a treatment instrument inserted into a treatment instrument channel.

The image pickup unit has a main part configured of an objective lens unit, an image pickup device, a substrate, and a cable. The objective lens unit includes one or a plurality of optical systems and a lens barrel configured to hold the one or the plurality of optical systems. The image pickup device is a CCD, a CMOS, or the like and configured to pick up an image inside a subject through the one or the plurality of optical systems. The substrate includes electronic components mounted thereon, and is electrically connected to the image pickup device. The cable is electrically connected to the substrate, and configured to transmit and receive electric signals to and from the substrate.

Furthermore, since the image pickup unit includes a plurality of members, as described above, the image pickup unit is configured to be long in a longitudinal axis direction of the insertion portion. In other words, the image pickup unit is constituted of a long unit.

In addition, the image pickup unit has a distal end fixed in a hole of a distal end constituting portion provided at a distal end in the longitudinal axis direction (hereinafter, just referred to as the distal end) of the insertion portion.

In order to provide a reduced diameter of a distal end side in the longitudinal axis direction (hereinafter, just referred to as the distal end side) of the insertion portion, a distal end of a treatment instrument channel is fixed in a hole, which is different from the above-described hole, of the distal end constituting portion, to thereby achieve an arrangement in which the treatment instrument channel is side by side with the image pickup unit in a radial direction of the insertion portion.

The image pickup unit and the treatment instrument channel have large outer dimensions, and occupy a large space inside the distal end of the insertion portion. The closer the image pickup unit and the treatment instrument channel are to each other in the radial direction, the smaller the diameter of the distal end side of the insertion portion can be achieved. A further reduction in a diameter of an insertion portion of an endoscope is desired particularly for a bronchoscope, a cystoscope, an ureteroscope, and the like.

SUMMARY

An endoscope according to one aspect of the present disclosure includes: a distal end constituting portion that is: provided at a distal end in a longitudinal axis direction of an insertion portion configured to be inserted into a subject, and includes a first hole and a second hole adjacent to the first hole; a treatment instrument channel including a distal end in the longitudinal axis direction that is fixed in the first hole; and an adjacent unit including a distal end in the longitudinal axis direction that is fixed in the second hole. The adjacent unit is arranged side by side with the treatment instrument channel in a radial direction of the insertion portion. The treatment instrument channel includes a first wall portion formed by compression forming such that a wall thickness of the first wall portion is smaller than a wall thickness of a different part of the treatment instrument channel. The first wall portion is disposed on a side of the treatment instrument channel that faces the adjacent unit in the radial direction.

In addition, an insertion portion of an endoscope according to one aspect of the present disclosure includes: the distal end constituting portion, the treatment instrument channel, and the adjacent unit.

A method of manufacturing an endoscope according to one aspect of the present disclosure is a method including: forming a first wall portion of a treatment instrument channel by compression forming such that a wall thickness of the first wall portion is smaller than a wall thickness of a different wall portion of the treatment instrument channel; positioning and fixing a distal end of the treatment instrument channel in the longitudinal axis direction in the first hole such that the first wall portion is adjacent to the second hole in the radial direction of the insertion portion; and fixing a distal end of an adjacent unit in the longitudinal axis direction in the second hole such that the adjacent unit is arranged side by side with the treatment instrument channel in the radial direction of the insertion portion

DETAILED DESCRIPTION OF THE PREFERRED EMBODIMENT(S)

Figure 1:
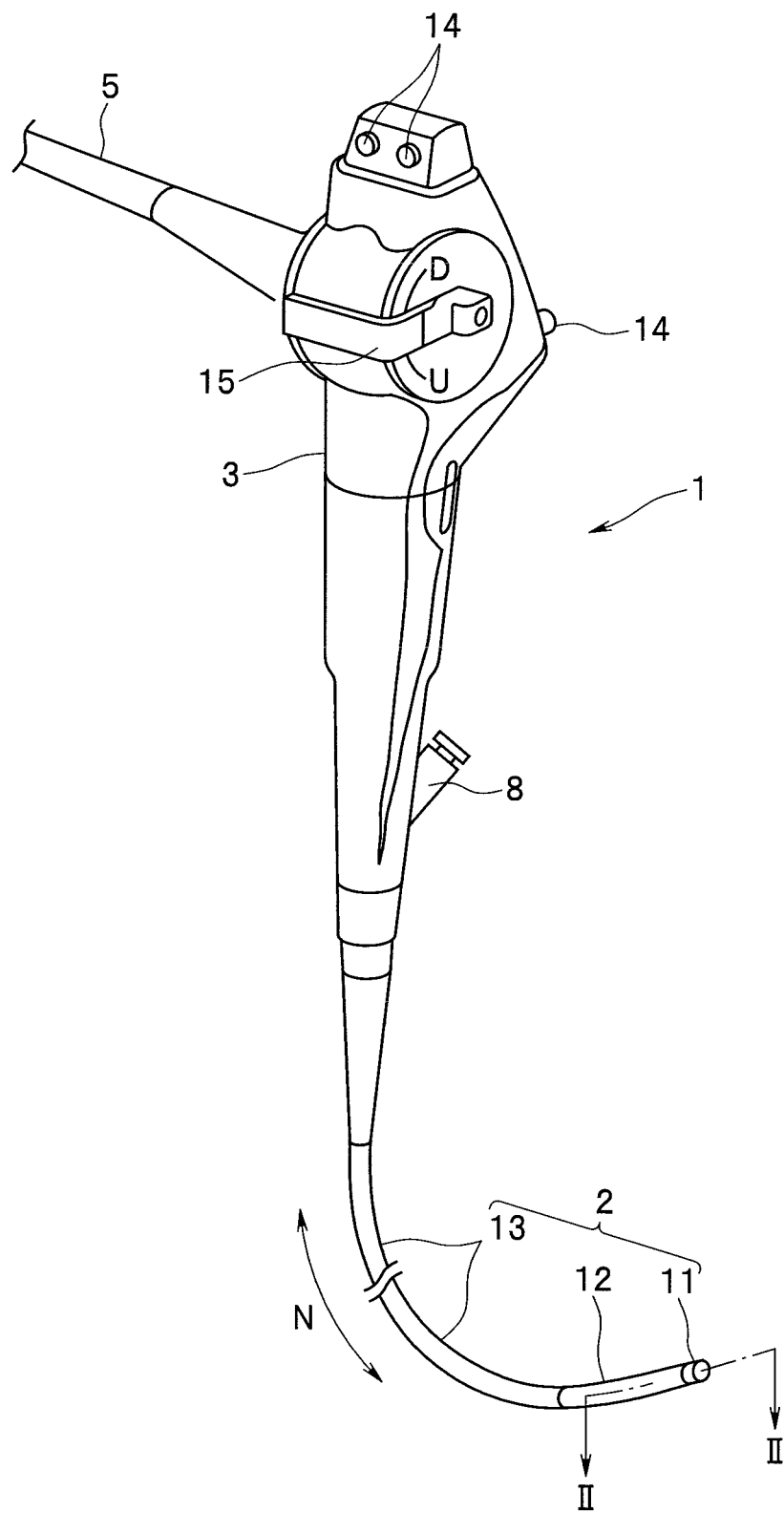
FIG. 1 is a partial perspective view showing an endoscope according to an exemplary embodiment.

In a known configuration of an endoscope, a treatment instrument channel can be formed so as to have a substantially D-shaped cross section by cutting out a part of an outer circumferential surface of the treatment instrument channel originally having a substantially circular cross section, the cut-out part being on a side close to the image pickup unit in a radial direction.

With such a configuration, the treatment instrument channel can be arranged closer to the image pickup unit in the radial direction by the amount of the cut-out part, compared with the conventional configuration. Therefore, the diameter of the distal end side of the insertion portion can be further reduced.

The treatment instrument channel is generally configured of a flexible tube or the like, so as to follow bending of a bending portion provided at the insertion portion, without interfering with the bending of the bending portion.

However, in the case where the image pickup unit and the treatment instrument channel are arranged side by side so as to be close to each other in the radial direction, the treatment instrument channel may be brought into contact with the image pickup unit in a part other than the distal end constituting portion in the longitudinal axis direction, due to sagging of the treatment instrument channel accompanying the bending of the bending portion and a partial deformation of the treatment instrument channel caused by the rigid treatment instrument being inserted into a relatively soft treatment instrument channel.

The above-described problem exists not only in the image pickup unit but also in long units (e.g., adjacent units to the treatment instrument channel), such as a known optical fiber bundle for illumination and the like, which are arranged side by side with the treatment instrument channel in the radial direction.

In view of such a circumstance, there is another known configuration of an endoscope including a treatment instrument channel having a forming portion formed by covering an outer circumference of a tube with a rigid material and squeezing the rigid material such that the rigid material is made to bite into the outer circumference of the tube.

With such a configuration, an outer diameter of the treatment instrument channel is reduced at the part covered with the rigid material and the part is hardened. Therefore, such a configuration is capable of preventing the long unit from being damaged due to the deformation of the treatment instrument channel while achieving the reduced diameter of the distal end side of the insertion portion.

Generally, in the above configuration and the like, since a rigid material is additionally used to form a forming portion which constitutes a part of a treatment instrument channel, a shape of the forming portion made of the rigid material is not uniform. As in such a configuration, even if the forming portion is formed in a part other than a distal end constituting portion, the forming portion is possibly brought into contact with a long unit located close to the forming portion.

In view of the above, the present disclosure is capable of providing an endoscope, an insertion portion of the endoscope, and a manufacturing method of the endoscope, which achieve a configuration for improving a durability of a long unit by preventing a damage on the long unit due to deformation of a treatment instrument channel while providing a reduced diameter of a distal end side of the insertion portion.

Hereinafter, embodiments of the present disclosure will be described with reference to drawings. In the embodiments to be described below, description will be made by taking a case where an endoscope is a bronchoscope, as an example.

FIG. 1 is a partial perspective view showing an endoscope of the present embodiment.

As shown in FIG. 1, an endoscope 1 includes a main part configured of an insertion portion 2, an operation portion 3, a universal cord 5, and a connector not shown. The insertion portion 2 is flexible and elongated along a longitudinal axis direction N, and configured to be inserted into a subject. The operation portion 3 is provided on a proximal end side in the longitudinal axis direction N (hereinafter, just referred to as the proximal end side) of the insertion portion 2. The universal cord 5 is extended from the operation portion 3. The connector is provided at an extension end of the universal cord and configured to be connected to an image processing apparatus, a light source apparatus, etc., not shown.

The insertion portion 2 has a main part including a distal end portion 11, a bending portion 12, and a flexible tube portion 13 in this order from the distal end side. The bending portion 12 is provided on a proximal end side of the distal end portion 11 and configured to be bendable in a plurality of directions, for example, two directions. The flexible tube portion 13 is pliable and flexible, and provided on a proximal end side of the bending portion 12. The bending portion 12 may be configured to be bendable in three or more directions.

In addition, the operation portion 3 includes, on a distal end side thereof, a treatment instrument insertion pipe sleeve 8 which serves as an insertion port through which various treatment instruments are inserted into a treatment instrument channel 40 to be described later (see FIG. 2).

The treatment instrument channel 40 is open on a distal end surface of the distal end portion 11. Various treatment instruments inserted from the treatment instrument insertion pipe sleeve 8 into the treatment instrument channel 40 are protruded from an opening of the distal end portion 11 into an inside of a subject.

Furthermore, the operation portion 3 includes, on a proximal end side thereof, a remote switch 14, a bending operation lever 15, and the like. The remote switch 14 is configured to give an image control instruction, such as freeze, release, etc., an instruction for suction through the treatment instrument channel, and the like. The bending operation lever 15 is used for bending operation of the bending portion 12.

Figure 3:
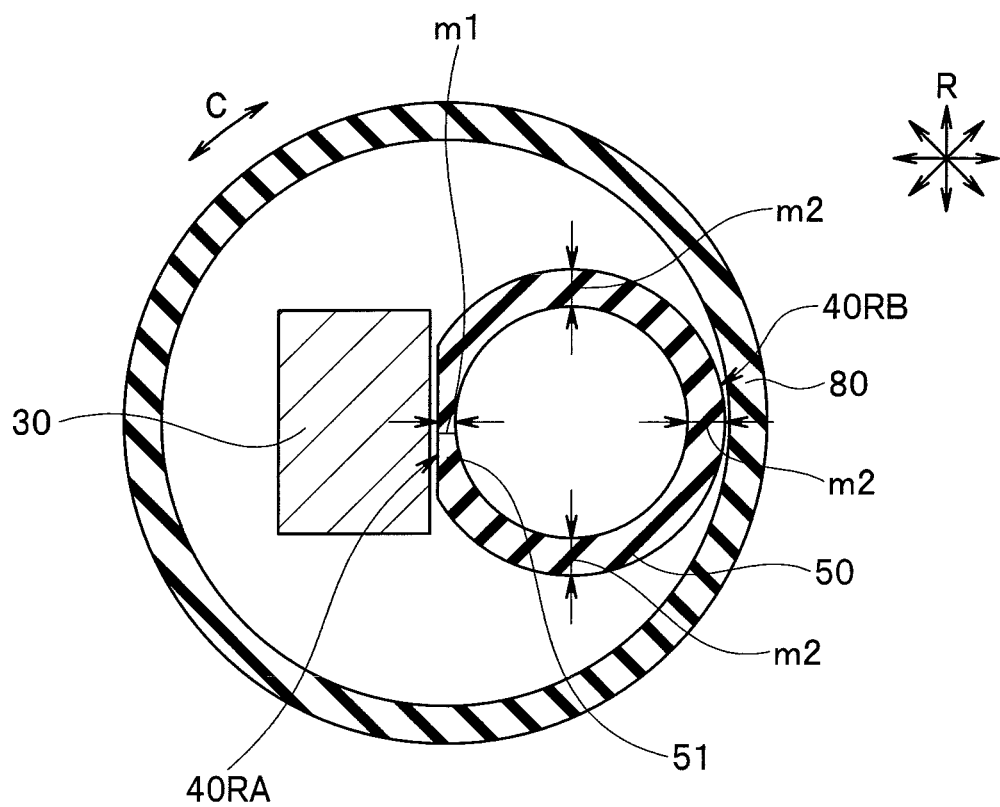
FIG. 3 is a cross-sectional view of a distal end portion taken along the line III-III in FIG. 2.
Figure 4:
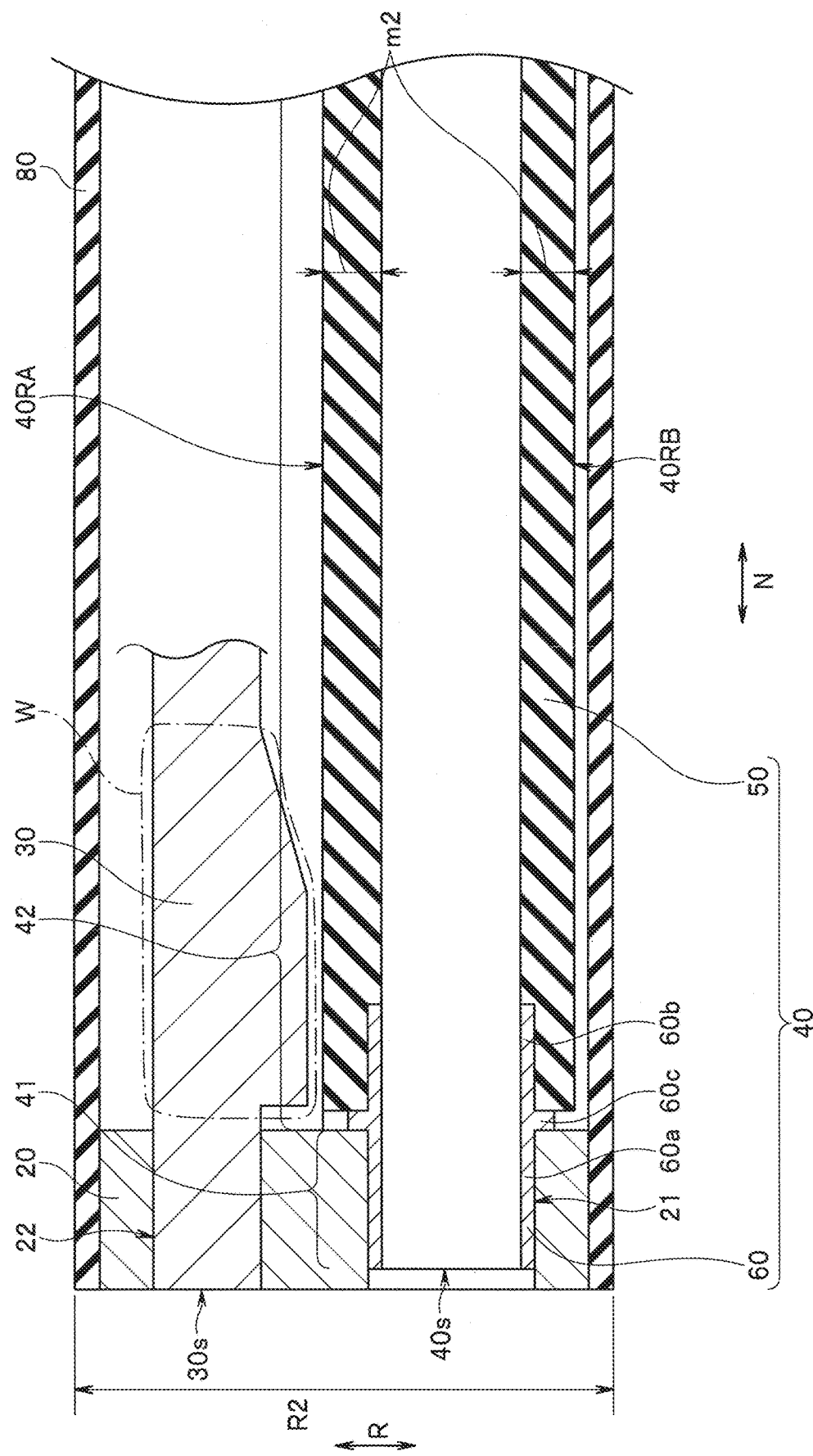
FIG. 4 is a partial cross-sectional view showing a configuration of a distal end side of an insertion portion of a conventional endoscope.

Next, description will be made on the configuration of the distal end side of the insertion portion 2, with reference to FIGS. 2 to 4. FIG. 2 is a partial cross-sectional view of the distal end side of the insertion portion taken along the line II-II in FIG. 1, FIG. 3 is a cross-sectional view of the distal end portion taken along the line III-III in FIG. 2, and FIG. 4 is a partial cross-sectional view showing a configuration of a distal end side of an insertion portion of a conventional endoscope.

Hereinafter, for simplification of the description and drawings, FIGS. 2 to 4 each show a configuration by taking a case in which only an image pickup unit 30 and the treatment instrument channel 40 are disposed inside the distal end of the insertion portion 2, as an example. However, various known members, which are normally included in the insertion portion of the endoscope, are actually provided together with the image pickup unit 30 and the treatment instrument channel 40.

Figure 2:
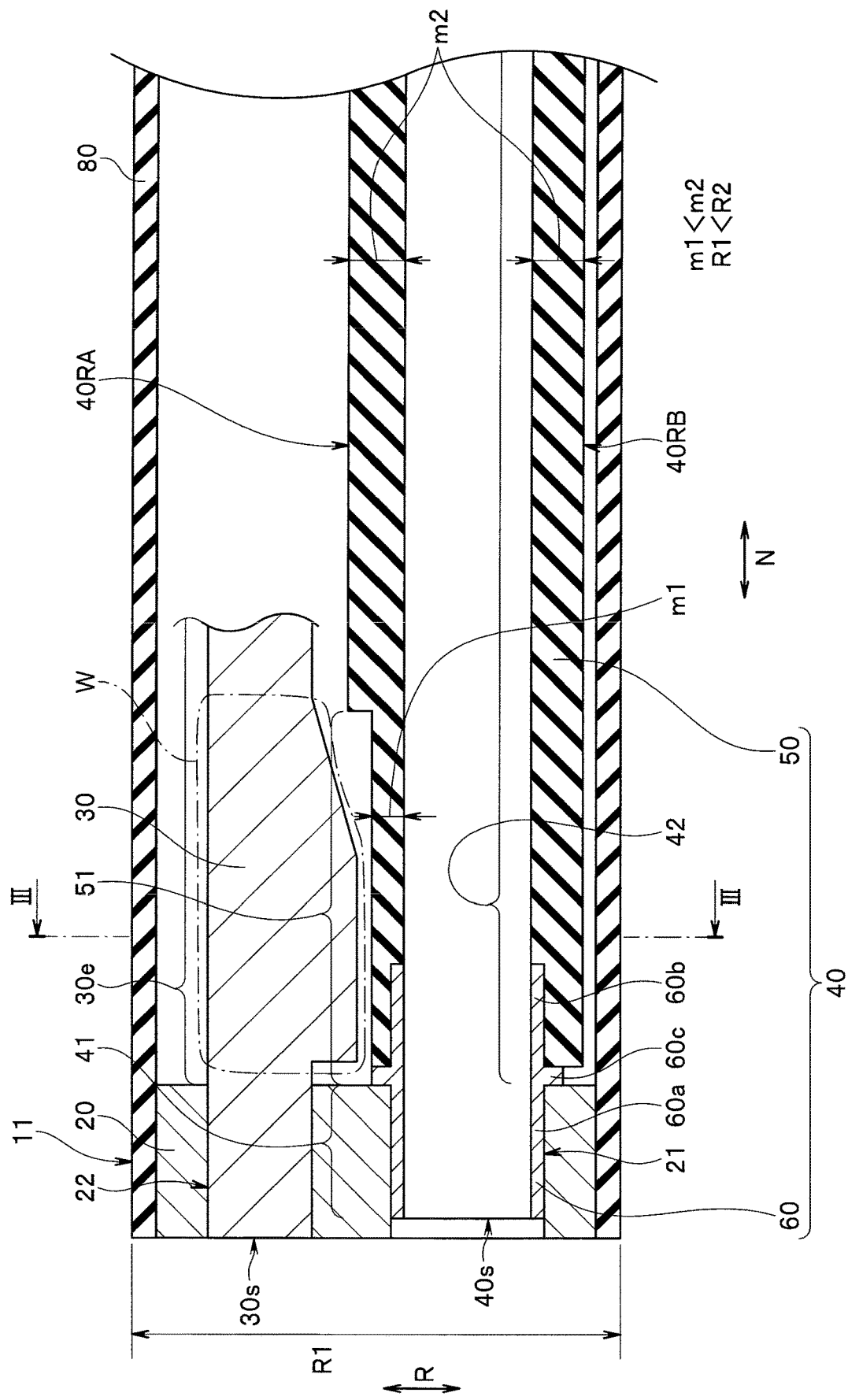
FIG. 2 is a partial cross-sectional view of a distal end side of an insertion portion taken along the line II-II in FIG. 1.

As shown in FIG. 2, a distal end constituting portion 20 is provided in the distal end portion 11 located at the distal end of the insertion portion 2. Note that a distal end side of a covering member 80 constituting an outer cover of the insertion portion 2 is fixed to an outer circumference of the distal end constituting portion 20.

In the distal end constituting portion 20, a first hole 21 and a second hole 22 are formed. The first and second holes penetrate through the distal end constituting portion 20 in the longitudinal axis direction N.

A distal end 40s of the treatment instrument channel 40 is fixed in the first hole 21, and a distal end 30s of the image pickup unit 30, which is a long unit (adjacent unit), is fixed in the second hole 22. As a result, the image pickup unit 30 is arranged side by side with the treatment instrument channel 40 inside the distal end of the insertion portion 2.

Note that the image pickup unit 30 and the treatment instrument channel 40 are arranged closely to each other in a radial direction R of the insertion portion 2 in order to reduce the diameter of the distal end side of the insertion portion 2.

The image pickup unit 30 has a main part including an objective lens unit, an image pickup device, a substrate, and a cable. The objective lens unit includes one or a plurality of optical systems and a lens barrel configured to hold the one or the plurality of optical systems. The image pickup device is a CCD, CMOS, or the like and configured to pick up an image of an inside of the subject with the one or the plurality of optical systems. The substrate includes electronic components mounted thereon and is electrically connected to the image pickup device. The cable is electrically connected to the substrate and configured to transmit and receive electric signals to and from the substrate. Note that, in the present embodiment, the simplified configuration of the image pickup unit 30 is shown for simplification of the drawings.

The treatment instrument channel 40 includes a first part 41 that is inserted in the first hole 21, and a second part 42 extending in the longitudinal axis direction N from the first hole 21 to the outside of the first hole 21.

The treatment instrument channel 40 has a main part including a soft tube 50 and a fixing pipe sleeve 60 for fixing the distal end of the treatment instrument channel 40 in the first hole 21. Note that the tube 50 and the fixing pipe sleeve 60 may be integrally formed of a resin material, for example.

The fixing pipe sleeve 60 has a main part including a distal-end-side portion 60a inserted in the first hole 21 and fixed therein, a protrusion 60c circumferentially protruded outward in the radial direction R on the outer circumferential surface of the fixing pipe sleeve 60, and a proximal-end-side portion 60b having an outer circumference to which the distal end side of the tube 50 is fixed.

In the present embodiment, the distal-end-side portion 60a constitutes the first part 41, and the protrusion 60c, the proximal-end-side portion 60b, and the tube 50 constitute the second part 42.

In addition, the distal-end-side portion 60a is inserted into the first hole 21 until the protrusion 60c abuts against the proximal end in the longitudinal axis direction (hereinafter, just referred to as the proximal end) of the distal end constituting portion 20.

Furthermore, the tube 50 is fixed to the outer circumference of the proximal-end-side portion 60b, with the distal end of the tube 50 being abutted against the protrusion 60c.

As shown in FIGS. 2 and 3, the configuration of the tube 50 is different from the conventional configuration as shown in FIG. 4, and the tube 50 includes a first forming portion 51 (first wall portion) formed on a part of a side 40RA which is close to the image pickup unit 30 in the radial direction R.

Specifically, the first forming portion 51 is formed on the distal end side of the tube 50 so as to be located in a region in the longitudinal axis direction N. The region is adjacent to a fragile portion W in the radial direction R. The fragile portion W is included in an extending portion 30e of the image pickup unit 30, the extending portion 30e extending in the longitudinal axis direction N from the second hole 22 to the outside of the second hole 22.

In other words, in the present embodiment, the first forming portion 51 is formed only in the second part 42. Note that the fragile portion W is a portion of the image pickup unit 30, such as the substrate on which electric components are mounted, the portion being rigid but fragile when in contact with other components.

The first forming portion 51 is formed by compression forming such that a wall thickness m1 of the tube 50 is smaller than a wall thickness m2 of other parts of the tube 50 (m1<m2).

As a result, the first forming portion 51 is more hardened than the other parts of the tube 50. Accordingly, the first forming portion 51 has high rigidity. In addition, the first forming portion 51 has a smaller diameter in the radial direction R than the diameter of the other parts of the tube 50. In other words, the first forming portion 51 formed on the tube 50 is a recessed part formed on a part of the outer circumference of the fragile portion W.

In addition, in the tube 50, at least the first forming portion 51 is made of a polymer material that can be subjected to compression forming.

Note that at least the first forming portion 51 may be made of a non-polymer material, as long as the non-polymer material can be subjected to compression forming.

Furthermore, the first forming portion 51 may be made of a material, such as PTFE (polytetrafluoroethylene), having a porous fine structure including a porous layer, for ease of the compression forming.

An example of the compression forming is thermal compression. With thermal compression, the shape of the first forming portion 51 can be made uniform in the radial direction R and along the circumferential direction C. Specifically, the wall thickness m1 of the part where the first forming portion 51 is formed can be made uniform along the longitudinal axis direction N.

Since other configurations of the endoscope 1 is the same as those of the conventional endoscope, descriptions thereof will be omitted.

Next, a manufacturing method of the endoscope 1 will be described with reference to FIG. 5. Specifically, description will be made on a method of fixing the treatment instrument channel 40 in the first hole 21 of the distal end constituting portion 20 and fixing the image pickup unit 30 in the second hole 22 of the distal end constituting portion 20.

Figure 5:
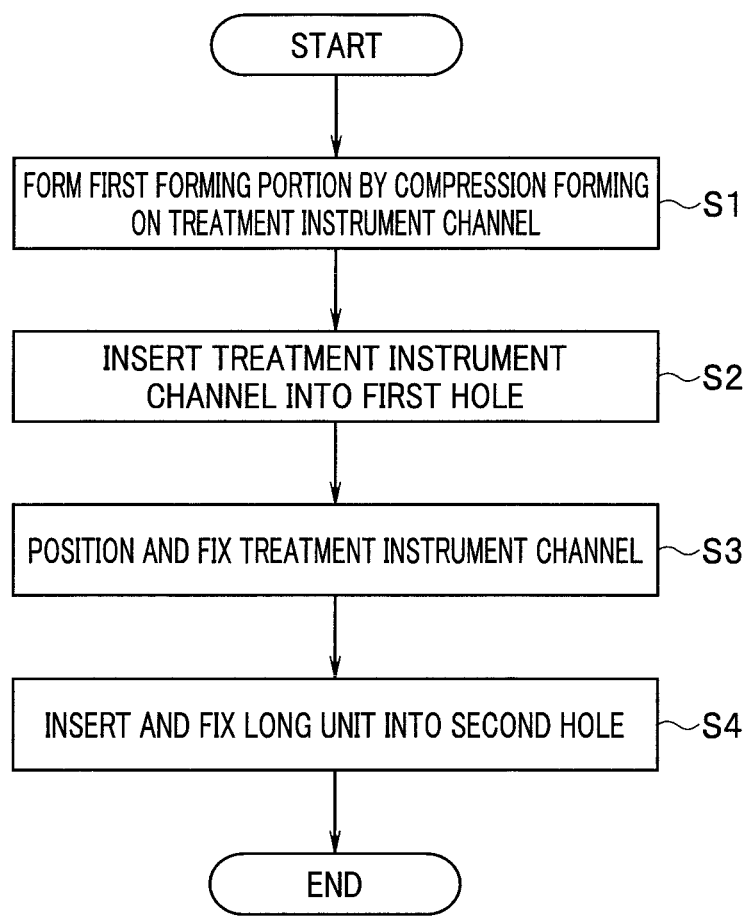
FIG. 5 is a process chart showing a manufacturing method of the endoscope according to an exemplary embodiment.

FIG. 5 is a process chart showing the manufacturing method of the endoscope in the present embodiment.

Initially, as shown in the step S1 in FIG. 5, a worker forms the first forming portion 51 by compression forming on the tube 50. The first forming portion 51 is formed in one part of the one side of the treatment instrument channel 40 in the radial direction R, specifically, in a part of the distal end side of the treatment instrument channel 40 in the circumferential direction C, such that the wall thickness m1 is smaller than the wall thickness m2 of other parts of the treatment instrument channel 40.

Next, in the step S2, the worker inserts the distal end side of the treatment instrument channel 40 into the first hole 21 of the distal end constituting portion 20.

Specifically, the worker inserts the distal-end-side portion 60a of the fixing pipe sleeve 60, with the tube 50 being fixed to the proximal-end-side portion 60b, into the first hole 21 until the protrusion 60c abuts against the proximal end of the distal end constituting portion 20.

After that, in the step S3, the worker positions the treatment instrument channel 40 in the circumferential direction C such that the first forming portion 51 is adjacent to the second hole 22 in the radial direction R, to fix the distal end 40s in the first hole 21.

Finally, in the step S4, the worker inserts the distal end side of the image pickup unit 30 into the second hole 22, and fixes the distal end 30s of the image pickup unit 30 in the second hole 22 such that the image pickup unit 30 is arranged side by side with the treatment instrument channel 40 in the radial direction R.

Since other steps of the manufacturing method of the endoscope 1 is the same as those in the conventional method, descriptions thereof will be omitted.

Thus, in the present embodiment, the first forming portion 51 is formed on the distal end side of the tube 50 in the region in the longitudinal axis direction N. The region is located on the side 40RA which is close to the image pickup unit 30 in the radial direction R and adjacent to the fragile portion W of the extending portion 30e of the image pickup unit 30 in the radial direction R.

In addition, the first forming portion 51 is formed by compression forming such that the wall thickness m1 becomes smaller than the wall thickness m2 of the other parts of the tube 50 (m1<m2). The first forming portion 51 has the rigidity higher than that of the other parts of the tube 50. Furthermore, the first forming portion 51 has the smaller diameter in the radial direction R than the diameter of the other parts of the tube 50.

In addition, the first forming portion 51 is formed by thermal compression.

According to such a configuration, in the part of the treatment instrument channel 40 where the first forming portion 51 is formed, the distance between the center of treatment instrument channel 40 and the center of the image pickup unit 30 in the radial direction R can be reduced by the difference between the thickness m2 and the thickness m1 (m2−m1).

Such a configuration enables the treatment instrument channel 40 and the image pickup unit 30 to be arranged more closely to each other in the radial direction R.

With such a configuration, the diameter R1 of the distal end side of the insertion portion 2 (the distal end sides of the distal end portion 11 and the bending portion 12) can be made smaller than a diameter R2 of the distal end side of the insertion portion 2 in a case where the treatment instrument channel 40 which is not provided with the first forming portion 51 and has the wall thickness m2 that is uniform in the longitudinal axis direction N is arranged as shown in FIG. 4 (R1<R2). Accordingly, the diameter of the distal end side of the insertion portion 2 can be more reduced.

In addition, the rigid first forming portion 51 is formed in the region of the tube 50, the region being close to the fragile portion W of the image pickup unit 30 in the radial direction R. Therefore, the first forming portion 51 can effectively prevent the tube 50 from contacting the fragile portion W due to sagging of the tube 50 following the bending of the bending portion 12 and deformation of the tube 50 by the treatment instrument inserted into the treatment instrument channel 40.

Furthermore, the first forming portion 51 is formed by thermal compression, which enables the wall thickness m1 to be uniform along the longitudinal axis direction N. Such a configuration can prevent a potential problem that the first forming portion 51 comes into contact with the fragile portion W, which may occur in the case where the shape of the first forming portion 51 is not uniform.

As described above, the present embodiment is capable of providing the endoscope 1, the distal end portion 11, and the manufacturing method of the endoscope 1, which achieve the configuration in which the durability of the long unit can be improved by preventing the damage on the long unit due to the deformation of the treatment instrument channel 40, while providing the reduced diameter of the distal end side of the insertion portion 2.

Figure 6:
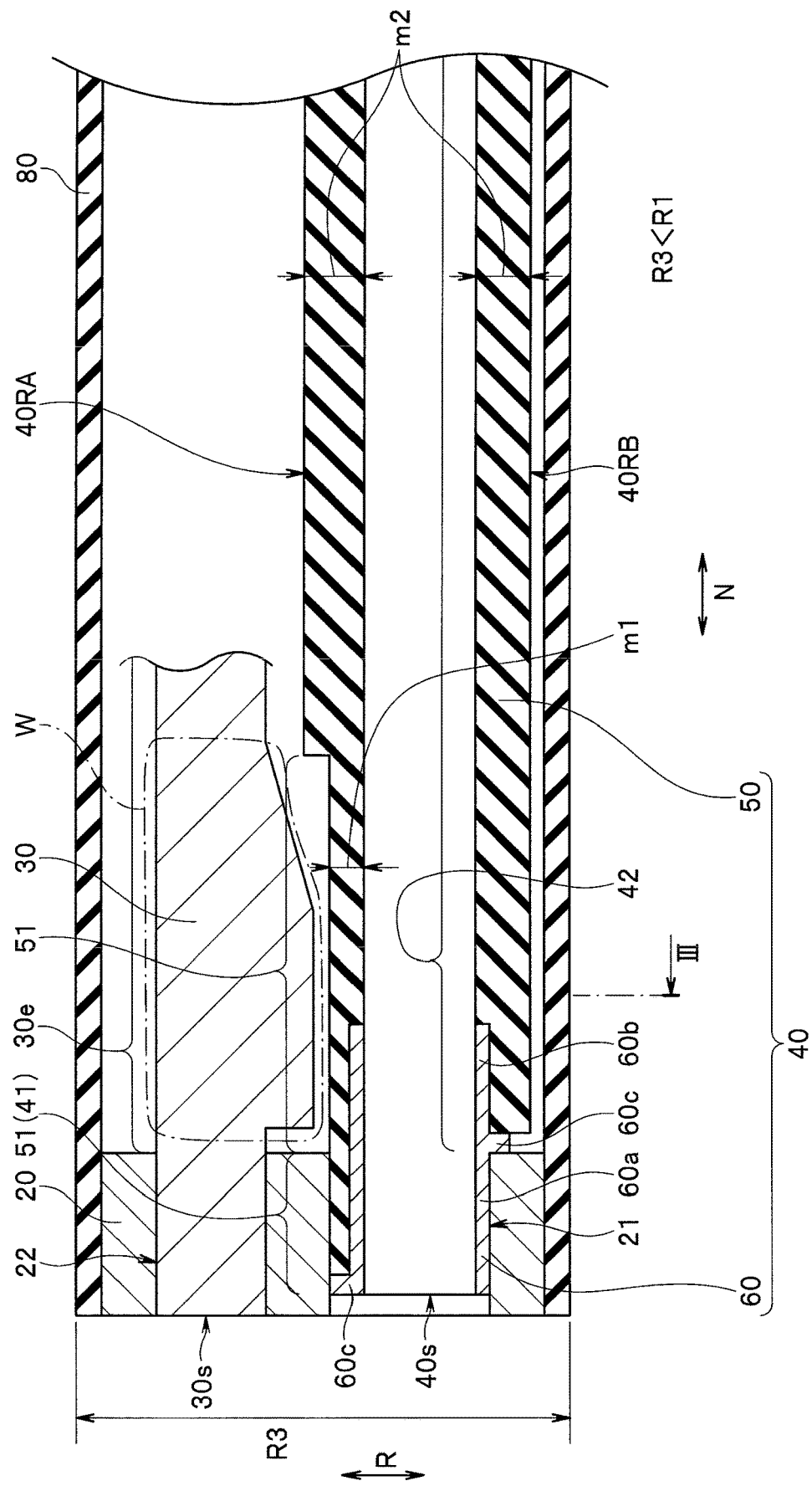
FIG. 6 is a partial cross-sectional view of a distal end side of an insertion portion of an endoscope according to an exemplary embodiment.

FIG. 6 is a partial cross-sectional view of a distal end side of an insertion portion of an endoscope according to another exemplary embodiment.

A configuration of the endoscope, the insertion portion of the endoscope, and a manufacturing method of the endoscope according to the present embodiment are different from those in the above embodiment shown in FIGS. 1 to 5 in that a first forming portion is formed also in a first part.

Therefore, only the different point will be described, and the same constituent elements as those in the above-described embodiment are attached with the same reference numerals and description thereof will be omitted.

As shown in FIG. 6, in the present embodiment, a distal end side of a tube 50 and a distal end side of a fixing pipe sleeve 60 are inserted in a first hole 21 and fixed therein.

Similarly as in the above-described embodiment, on the distal end side of the tube 50, a first forming portion 51 is formed in a distal end region of a side 40RA which is close to the image pickup unit 30.

In other words, the first forming portion 51 is formed not only in a second part 42 but also in a first part 41. Therefore, the shape of the fixing pipe sleeve 60 is also different from that in the above embodiment. On the side 40 RA of the outer circumference of the treatment instrument channel 40, the fixing pipe sleeve 60 includes, at the distal end thereof, a protrusion 60c against which the distal end of the tube 50 is abutted.

Note that the tube 50 and the fixing pipe sleeve 60 may be integrally formed of a resin material, for example.

In the present configuration, instead of the protrusion 60c, a protrusion against which the distal end of the tube 50 is abutted may be formed in the first hole 21. In this case, the treatment instrument channel 40 can be positioned by causing the distal end of the tube 50 to abut against the protrusion in the first hole 21. Therefore, such a configuration eliminates the need for providing the fixing pipe sleeve 60 at the distal end of the tube 50.

Note that other configurations are the same as those in the above-described embodiment described with respect to FIGS. 1 to 5.

In addition, the method of inserting and fixing the distal end side of the treatment instrument channel 40 in the first hole 21 is the same as that in the above embodiment, other than inserting the first forming portion 51 into the first hole 21 and fixing the distal end 40s in the first hole 21.

With such a configuration, the first forming portion 51 is formed also in the first part 41. Therefore, a diameter R3 of the distal end side of the insertion portion 2 can be made smaller in the radial direction R by the recessed amount of the first forming portion 51 than the diameter R1 in the above embodiment described with respect to FIGS. 1 to 5 (R3<R1).

Note that other configurations are the same as those in the above-described embodiment.

In the above-described present embodiment, the first forming portion 51 is formed both in the first part 41 and the second part 42.

The configuration of the first forming portion 51 is not limited to the above-described one, but the first forming portion 51 may be formed only in the first part 41, if the objective of the first forming portion is only to reduce the diameter of the distal end side of the insertion portion 2, i.e., the diameter of the distal end portion 11 in this case, in other words, if the objective for preventing the treatment instrument channel 40 from contacting the fragile portion W of the image pickup unit 30 may be ignored.

Figure 7:
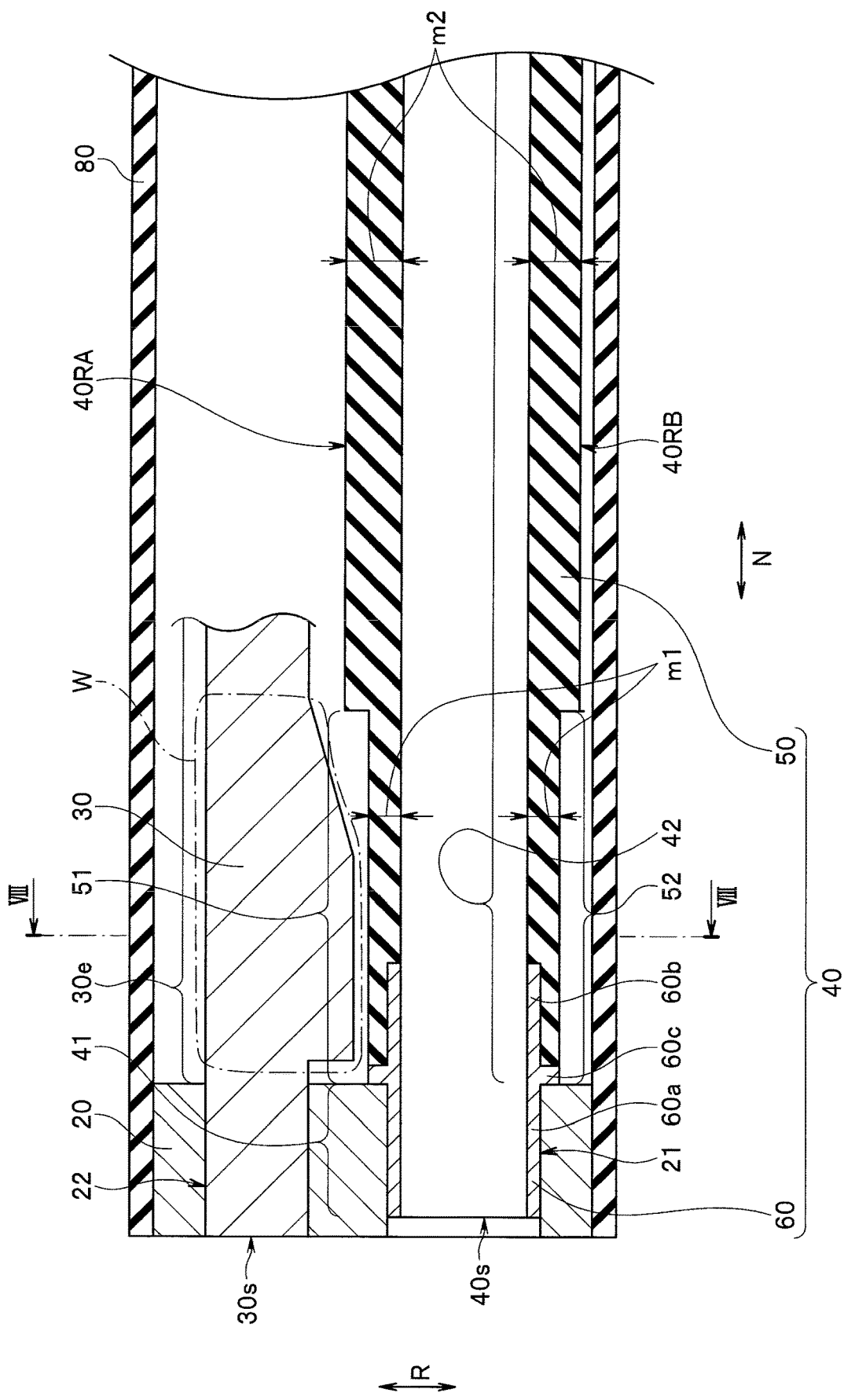
FIG. 7 is a partial cross-sectional view of a distal end side of an insertion portion of an endoscope according to an exemplary embodiment.
Figure 8:
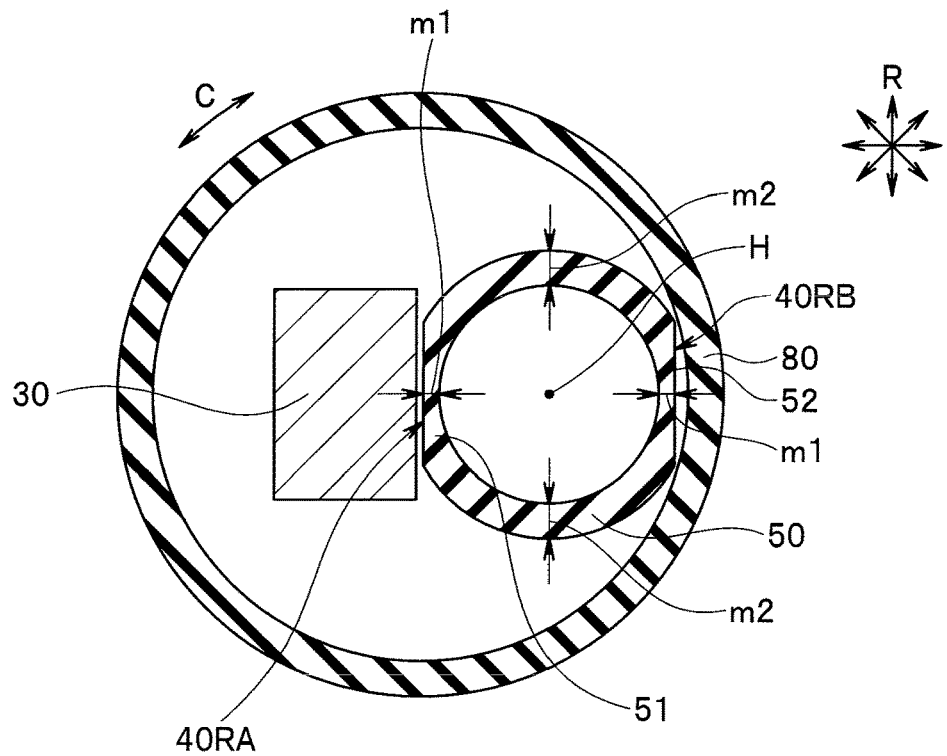
FIG. 8 is a cross-sectional view of a distal end portion taken along the line VIII-VIII in FIG. 7.

FIG. 7 is a partial cross-sectional view of a distal end side of an insertion portion of an endoscope according to another exemplary embodiment. FIG. 8 is a cross-sectional view of a distal end portion taken along the line VIII-VIII in FIG. 7.

A configuration of the endoscope, an insertion portion of the endoscope, and a manufacturing method of the endoscope according to the present embodiment are different from those in the above embodiment as shown in FIGS. 1 to 5 in that a treatment instrument channel includes a second forming portion formed at a position different from the position of the first forming portion in the radial direction such that a wall thickness of the part where the second forming portion is formed is the same as that of the part where the first forming portion is formed.

Therefore, only the different point will be described, and the same constituent elements as those in the above-described embodiment are attached with the same reference numerals and description thereof will be omitted.

As shown in FIGS. 7 and 8, in the present embodiment, the tube 50 includes a second forming portion 52 formed only in a second part 42 at the position different from the position of the first forming portion 51 in the radial direction R.

Specifically, the second forming portion 52 is formed on the tube 50 on a side 40RB in the radial direction R so as to be located at a position symmetric to the first forming portion 51 around a center axis H of the treatment instrument channel 40.

More specifically, as shown in FIG. 8, the second forming portion 52 is formed in the insertion portion 2 so as to be located on a side close to a covering member 80 of the tube 50 in the radial direction R.

The second forming portion 52 is formed by compression forming such that a wall thickness m1 of the tube 50 becomes smaller than the wall thickness m2 of other parts of the tube 50.

Note that the thickness of the second forming portion 52 is not necessarily the same as that of the first forming portion 51. For example, the thickness of the second forming portion 52 may be smaller than that of the first forming portion 51. Alternatively, the thickness of the first forming portion 51 may be smaller than that of the second forming portion 52. In both cases, the diameter of the distal end side of the insertion portion 2 can be reduced. In addition, the method of forming the second forming portion 52 is the same as the method of forming the first forming portion 51.

Other configurations are the same as those in the above-described embodiment. Furthermore, the method of inserting and fixing the treatment instrument channel 40 in the first hole 21 is the same as that in the above embodiment.

With such a configuration, the two rigid portions, i.e., the first forming portion 51 and the second forming portion 52 are formed on the distal end side of the tube 50. Therefore, such a configuration is capable of more effectively preventing the treatment instrument channel 40 from sagging or deforming easily than the configuration in which only the first forming portion 51 is formed.

In addition, the diameter in the radial direction R of the distal end side of the insertion portion 2 can be reduced in each of the respective parts where the first forming portion 51 and the second forming portion 52 are formed by the difference between the wall thickness m2 and m1 (m2−m1).

Note that other configurations are the same as those in the above-described embodiment.

Also in the present embodiment, similarly as in the embodiment described above with respect to FIG. 6, the second forming portion 52 may be formed also in the first part 41. Alternatively, the second forming portion 52 may be formed only in the first part 41.

Figure 9:
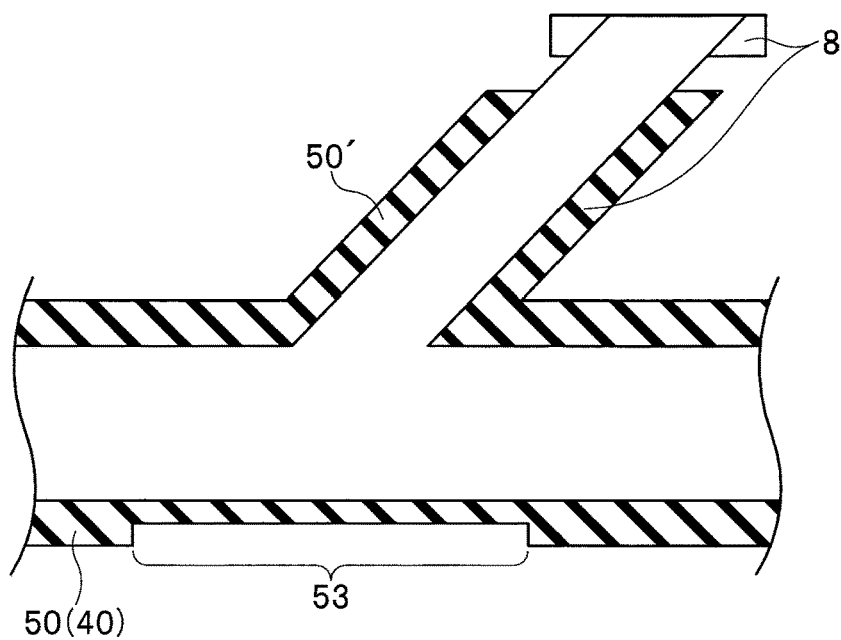
FIG. 9 is a partial cross-sectional view showing an exemplary embodiment in which a compression forming portion is formed at a branched position of a pipe sleeve for treatment instrument in a tube of a treatment instrument channel of the endoscope in FIG. 1.

Below, description will be made on a modification with reference to FIG. 9. FIG. 9 is a partial cross-sectional view showing a modification in which a compression forming portion is formed at a branched position of a pipe sleeve for treatment instrument in a tube of a treatment instrument channel of the endoscope in FIG. 1.

In the above embodiments, the first forming portion or the second forming portion is formed on the distal end side of the tube 50.

The configurations of the forming portions are not limited to the above-described embodiments, but a forming portion 53 which is formed by compression forming in the similar manner as for the first forming portion 51 and the second forming portion 52. The forming portion 53 may be formed on the tube 50 at a position opposed to a branch conduit 50' located at a branched position of a treatment instrument insertion pipe sleeve 8, as shown in FIG. 9.

With such a configuration, the forming portion 53 is capable of preventing the tube 50 from deforming at the above-described branched position by the treatment instrument inserted from the treatment instrument insertion pipe sleeve 8, and thereby prevent the tube 50 from contacting other long units.

In the above-described embodiments, description has been made by taking the case where the endoscope 1 is a bronchoscope as an example. However, the endoscope 1 is not limited to the bronchoscope. It is needless to say that the present disclosure can be applied to any endoscope, such as a cystoscope, an ureteroscope, and the like, as long as the diameter of the distal end side of the insertion portion 2 of the endoscope is required to be reduced.

Furthermore, in the above-described embodiments, description has been made by taking the case where the long unit is the image pickup unit 30 as an example. However, the long unit is not limited to the image pickup unit 30. It is needless to say that the present disclosure can be applied to any component, such as an optical fiber bundle for illumination, ultrasound transducer unit, and the like, as long as the component is arranged side by side with the treatment instrument channel 40 in the insertion portion 2 and is likely to be in contact with the treatment instrument channel 40.

In addition, the present disclosure is not limited to the above-described embodiments, but can be changed appropriately within a range not departing from the gist or concept of the disclosure that can be read from claims, throughout the specification, and the drawings.

What is claimed is:

1. An endoscope comprising:
a distal end constituting portion provided at a distal end in a longitudinal axis direction of an insertion portion configured to be inserted into a subject, the distal end constituting portion comprising a first hole and a second hole adjacent to the first hole;
a treatment instrument channel, a distal end of the treatment instrument channel in the longitudinal axis direction being fixed in the first hole; and
an adjacent unit that extends in the longitudinal axis direction and is arranged side by side with the treatment instrument channel in a radial direction of the insertion portion, the adjacent unit including a distal end that is fixed in the second hole, wherein
the treatment instrument channel comprises a first wall portion formed by compression forming such that a wall thickness of the first wall portion is smaller than a wall thickness of a different wall portion of the treatment instrument channel, the first wall portion being disposed on a side of the treatment instrument channel that faces the adjacent unit in the radial direction.

2. The endoscope according to claim 1, wherein at least the first wall portion is made of a polymer material.

3. The endoscope according to claim 2, wherein the first wall portion has a porous fine structure.

4. The endoscope according to claim 1, wherein
the treatment instrument channel comprises a first part inserted into the first hole and a second part extending proximally in the longitudinal axis direction from the first hole to an outside of the first hole, and
the first wall portion is formed in the second part.

5. The endoscope according to claim 4, wherein the first wall portion is also formed in the first part.

6. The endoscope according to claim 1, wherein
the treatment instrument channel includes a first part inserted into the first hole and a second part extending proximally in the longitudinal axis direction from the first hole to an outside of the first hole, and
the first wall portion is formed only in the second part.

7. The endoscope according to claim 1, wherein
the adjacent unit includes an extending portion extending proximally in the longitudinal axis direction from the second hole to an outside of the second hole, the extending portion including a fragile portion, and
the first wall portion is formed in a region in the longitudinal axis direction, the region being adjacent to the fragile portion in the radial direction.

8. The endoscope according to claim 7, wherein the first wall portion is a recess formed in a wall of the treatment instrument channel at a position that faces a part of an outer circumference of the fragile portion in the radial direction.

9. The endoscope according to claim 7, wherein the fragile portion includes a substrate on which an electronic component is mounted.

10. The endoscope according to claim 1, wherein the treatment instrument channel includes a second wall portion formed by compression forming such that the wall thickness of the second wall portion is smaller than the wall thickness of the different wall portion of the treatment instrument channel, the second wall portion being formed at a position different from a position of the first wall portion in the radial direction.

11. The endoscope according to claim 10, wherein the second wall portion is formed at a position symmetric to the first wall portion around a center axis of the treatment instrument channel in the radial direction.

12. The endoscope according to claim 11, wherein the second wall portion is formed on a side of the treatment instrument channel facing a covering member of the insertion portion in the radial direction.

13. The endoscope according to claim 10, wherein the second wall portion is formed on a side closer to a covering member of the insertion portion relative to the first wall portion.

14. The endoscope according to claim 1, wherein the adjacent unit is an image pickup unit configured to pick up an image of the subject, or an optical fiber bundle for illumination.

15. The endoscope according to claim 1, wherein the first wall portion has a higher rigidity than the different wall portion.

16. The endoscope according to claim 1, wherein the first wall portion is formed in a bendable portion of the insertion portion.

17. The endoscope according to claim 1, wherein the treatment instrument channel includes a first part inserted into the first hole and a second part extending proximally in the longitudinal axis direction from the first part so as to extend entirely outside of the distal end constituting part, and the first wall portion is formed only in the second part.

18. An insertion portion of an endoscope comprising:
a distal end constituting portion provided at a distal end in a longitudinal axis direction, the distal end constituting portion comprising a first hole and a second hole adjacent to the first hole;
a treatment instrument channel, a distal end of the treatment instrument channel in the longitudinal axis direction being fixed in the first hole; and
an adjacent unit that extends in the longitudinal axis direction and is arranged side by side with the treatment instrument channel in a radial direction of the insertion portion, the adjacent unit including a distal end that is fixed in the second hole, wherein
the treatment instrument channel comprises a first wall portion formed by compression forming such that a wall thickness of the first wall portion is smaller than a wall thickness of a different wall portion of the treatment instrument channel, the first wall portion being disposed on a side of the treatment instrument channel that faces the adjacent unit in the radial direction.

19. A method of manufacturing an endoscope, the endoscope comprising an insertion portion configured to be inserted into a subject and a distal end constituting portion provided at a distal end in a longitudinal axis direction of the insertion portion, the distal end constituting portion including a first hole and a second hole adjacent to the first hole, the method comprising:
forming a first wall portion in a treatment instrument channel by compression forming such that a wall thickness of the first wall portion is smaller than a wall thickness of a different wall portion of the treatment instrument channel, the first wall portion being disposed on one side of the treatment instrument channel in a radial direction of the insertion portion;
positioning and fixing a distal end of the treatment instrument channel in the longitudinal axis direction in the first hole such that the first wall portion is adjacent to the second hole in the radial direction of the insertion portion; and fixing a distal end of an adjacent unit in the longitudinal axis direction in the second hole such that the adjacent unit is arranged side by side with the treatment instrument channel in the radial direction of the insertion portion.

20. The method according to claim 19, wherein the first wall portion is formed by thermal compression.

* * * * *